United States Patent
Burger et al.

(10) Patent No.: US 9,131,896 B2
(45) Date of Patent: Sep. 15, 2015

(54) IN SITU OFFSET COMPENSATION FOR PRESSURE SENSORS

(75) Inventors: Juergen Burger, Neuchatel (CH); Toralf Bork, Neuchatel (CH)

(73) Assignee: MEDOS INTERNATIONAL S.A.R.L. (CH)

( * ) Notice: Subject to any disclaimer, the term of this patent is extended or adjusted under 35 U.S.C. 154(b) by 935 days.

(21) Appl. No.: 12/853,364

(22) Filed: Aug. 10, 2010

(65) Prior Publication Data

US 2011/0040206 A1    Feb. 17, 2011

Related U.S. Application Data

(60) Provisional application No. 61/233,395, filed on Aug. 12, 2009.

(51) Int. Cl.

| | |
|---|---|
| *A61B 5/00* | (2006.01) |
| *G01L 19/02* | (2006.01) |
| *G01L 27/00* | (2006.01) |
| *A61B 5/03* | (2006.01) |

(52) U.S. Cl.
CPC .............. *A61B 5/6846* (2013.01); *A61B 5/031* (2013.01); *G01L 19/02* (2013.01); *G01L 27/002* (2013.01); *A61B 5/0031* (2013.01); *A61B 5/032* (2013.01); *A61B 2560/0223* (2013.01); *A61B 2562/0247* (2013.01)

(58) Field of Classification Search
CPC . A61B 5/031; A61B 5/032; A61B 2562/0247
USPC ....................................................... 600/561
See application file for complete search history.

(56) References Cited

U.S. PATENT DOCUMENTS

| | | | |
|---|---|---|---|
| 4,206,762 A | 6/1980 | Cosman | |
| 4,237,900 A | 12/1980 | Schulman et al. | |
| 4,281,667 A | 8/1981 | Cosman | |
| 4,676,255 A | 6/1987 | Cosman | |
| 4,954,925 A | 9/1990 | Bullis et al. | |
| 5,142,912 A | 9/1992 | Frische | |
| 5,361,218 A | 11/1994 | Tripp et al. | |
| 5,444,901 A | 8/1995 | Wiegand et al. | |
| 5,493,470 A * | 2/1996 | Zavracky et al. | ............... 438/53 |
| 5,955,161 A | 9/1999 | Tropsha | |
| 6,295,365 B1 * | 9/2001 | Ota | ............... 381/114 |
| 7,413,547 B1 | 8/2008 | Lichtscheidl et al. | |
| 2001/0026111 A1 * | 10/2001 | Doron et al. | ............... 310/322 |
| 2009/0036754 A1 * | 2/2009 | Pons et al. | ............... 600/301 |

OTHER PUBLICATIONS

"Contiguous" dictionary.com, accessed Aug. 19, 2013.*
Brean et al.; *Comparison of Intracranial Pressure Measured Simultaneously Within the Brain Parenchyma and Cerebral Ventricles*; (2006); pp. 411-414; Journal of Clinical Monitoring and Computing 20: Springer 2006.
*Codman® ICP Monitoring System Quick set-up Guide*; Product Brochure © 2001 Codman & Shurtleff, Inc.

(Continued)

*Primary Examiner* — Devin Henson

(57) ABSTRACT

A pressure sensor having a substrate and a first, deformable membrane, partially supported by the substrate, which generates a first sensor reading when deformed by pressure. A second membrane is contiguous to the first membrane. When the second membrane is energized, it deforms the first membrane to alter the first sensor reading.

17 Claims, 5 Drawing Sheets

(56) References Cited

OTHER PUBLICATIONS

Seder et al.; *Multimodality Monitoring in Patients with Elevated Intracranial Pressure*; Intensive Care Medicine; 2008; pp. 811-821; Springer New York.

Steiner et al; *Monitoring the injured brain: ICP and CBF*, British Journal of Anaesthesia (2006) pp. 26-38; 97(1): Advance Access Publication May 12, 2006.

\* cited by examiner

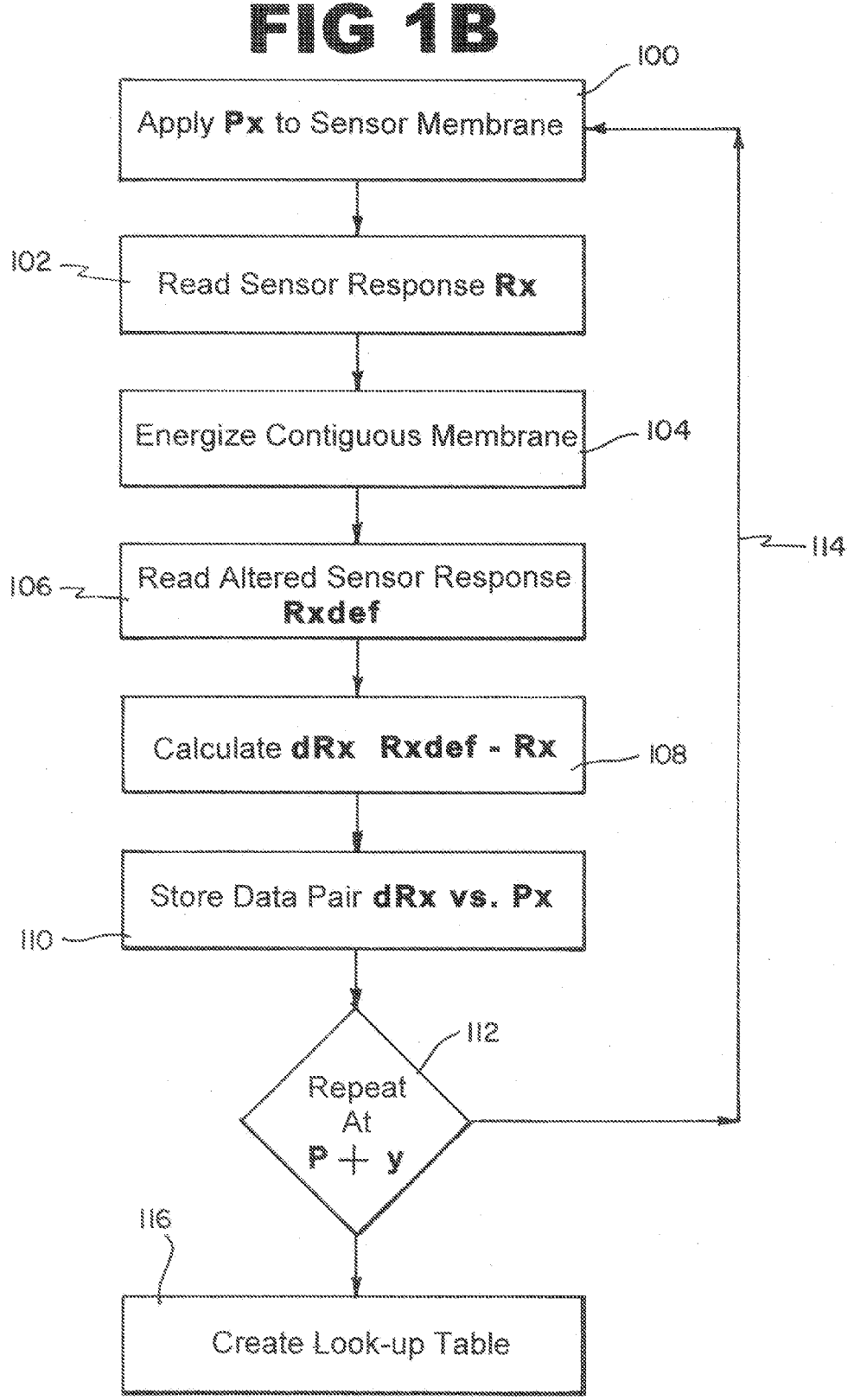

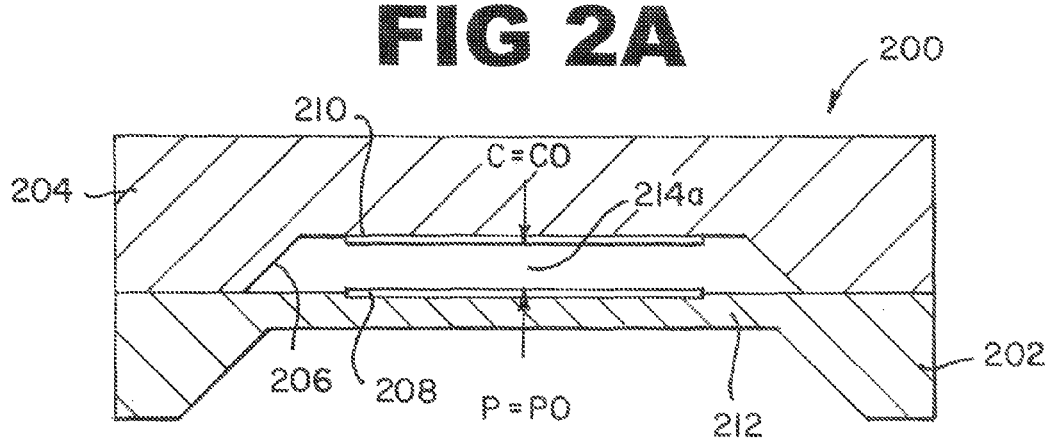
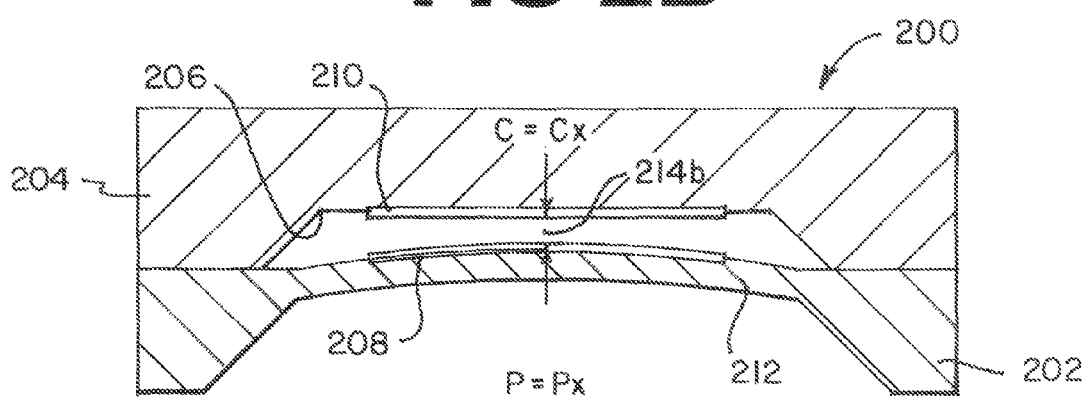
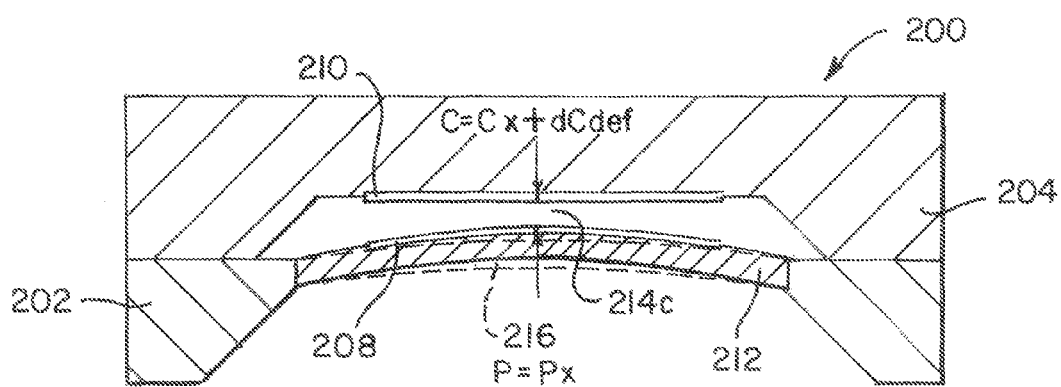

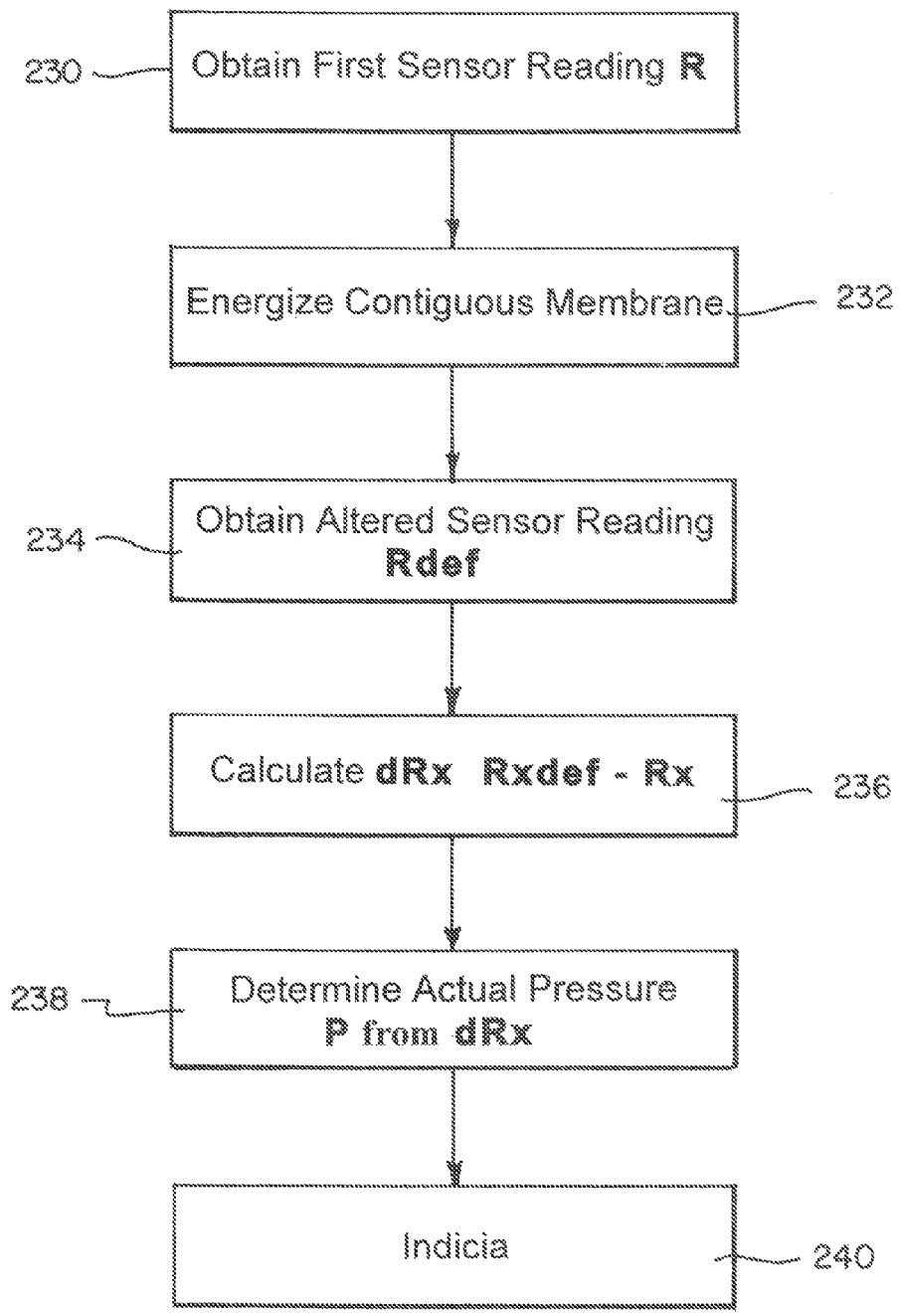

US 9,131,896 B2

IN SITU OFFSET COMPENSATION FOR PRESSURE SENSORS

CROSS-REFERENCE TO RELATED APPLICATION

This application claims priority to U.S. Provisional Application No. 61/233,395 by Burger et al. filed Aug. 12, 2009 entitled "Ultrathin Multilayers for a Hermetic Packaging".

BACKGROUND OF THE INVENTION

1. Field of the Invention

The invention relates to verification of output readings for pressure sensors and more particularly to pressure sensing compound membranes which are deformable both by ambient pressure and electrical activation.

2. Description of the Related Art

Human brain tissue includes gray and white matter suspended in cerebrospinal fluid within the cranium and nourished by blood delivered through cerebral arteries. The gray matter has closely spaced cell bodies of neurons, such as in the cerebral cortex, and the underlying white matter contains densely packed axons that transmit signals to other neurons. Brain tissue has different densities and comprises approximately eighty percent of the intracranial content, with blood and cerebrospinal fluid each normally comprising approximately ten percent.

Cerebrospinal fluid is produced at a rate of approximately 20 ml per hour by secretory cells in several connected chambers known as ventricles and typically is renewed four to five times per day. Cerebrospinal fluid in a healthy human flows slowly and continuously through the ventricles, propelled by pulsations of the cerebral arteries. The fluid then flows around the brain tissues and the spinal column, and through small openings into the arachnoid membrane, which is the middle layer of the meninges surrounding the brain parenchyma and ventricles, where the fluid is finally reabsorbed into the bloodstream.

Under normal conditions, bodily mechanisms compensate for a change in fluid volume within the cranium through tissue resilience and by adjusting the total volume of blood and cerebrospinal fluid so that a small increase in fluid volume does not increase intracranial pressure. Similarly, a healthy brain compensates for an increase in intracranial pressure to minimize a corresponding increase in intracranial volume. This volume- and pressure-relationship can be explained in terms of cerebral compliance, which term is intended to include herein the terms elastance and intracranial compliance.

The brain is compliant as long as a person's auto-regulatory mechanism can compensate for any change in volume. As soon as the brain's auto-regulation or compensatory mechanisms fail, or if too great a trauma to the head occurs, blood and cerebrospinal fluid cannot be displaced, and the brain can no longer adapt to any increase in fluid volume.

A reduction in cerebral compliance eventually will lead to an undesired increase in intracranial pressure, such as described by Seder et al. in "Multimodality Monitoring in Patients with Elevated Intracranial Pressure" from the book "Intensive Care Medicine" published by Springer New York (2008). Reduced cerebral compliance is also referred to as increased brain stiffness or as stiff brain. As more fluid volume is added, a threshold is reached beyond which small increases in volume lead to dramatic and unhealthy increases in intracranial pressure. Intracranial pressure can also increase due to secondary damage to the brain caused by hemorrhage, stroke, infection, tumor, or trauma from sports injuries, automobile accidents or other impacts to the head.

Intracranial pressure has been measured at a number of epi-dural and sub-dural locations, such as described by Steiner et al. in "Monitoring the injured brain: ICP and CBF", British Journal of Anaesthesia 97(1): 26-38 (2006) and by Brean et al. in "Comparison of Intracranial Pressure Measured Simultaneously Within the Brain Parenchyma and Cerebral Ventricles", Journal of Clinical Monitoring and Computing 20: 411-414 (2006). Implantable pressure sensors for intracranial pressure monitoring in Intensive Care Units and for long-term monitoring typically are based on deflection of thin membranes. The deflection typically is measured using capacitive or piezoresistive effects.

It is common for piezoelectric sensors such Codman™ MicroSensor pressure sensing probes which use an ASIC based half-bridge strain gauge technology, currently commercially available with ICP Express™ Monitor from Codman & Shurtleff, Inc. of Raynham, Mass., to be calibrated by personnel in the operating room or surgical suite by immersing the sensing probes in saline solution. This pre-implantation immersion corrects for drift which may be induced by water-uptake by polymeric materials used for biocompatible packaging, which can result in swelling effects, or mechanical relaxation effects due to contact with bodily fluids.

Other types of pressure sensors are zeroed during manufacture and the null point is transferred to a patient monitor which may introduce an error and increase the risk of a false pressure reading. Capacitive sensors suffer from drift due to electronic interference with fluids due to stray capacitive effects or changing electrical potentials of surrounding conductive bodily fluids.

Problems with sensor calibration and drift are described in a number of patents including U.S. Pat. Nos. 4,206,762 and 4,281,667 to Cosman, U.S. Pat. No. 4,954,925 to Bullis et al., U.S. Pat. No. 5,361,218 to Tripp et al. and U.S. Pat. No. 5,444,901 to Wiegand et al. An implantable sensor with separate reference circuit is disclosed in U.S. Pat. No. 7,413,547 to Lichtscheidl et al.

Two more recent examples of constructing allegedly self-calibrating pressure sensors, one relative to atmospheric pressure and the other absolute, are provided by Pons et al. in United States Patent Application Pub. No. 2009/0036754. In each example, an actuator is placed at a fixed distance from a deformable membrane of a sensor having at least one piezoelectric transducer, preferably two or four transducers. The sensor further includes a polarization contact such that an electrostatic force is exerted on the membrane when the actuator is charged. In other words, electrostatic actuation is used to deform the membrane in a defined way.

It is therefore desirable to verify the correct functioning of pressure sensors in situ and in an accurate, cost-effective, easy-to-use manner.

SUMMARY OF THE INVENTION

An object of the present invention is to provide accurate corrections of sensors while minimizing handling errors in the operating room and during use of the sensors in situ.

Another object of the present invention is to enable automatic correction of sensor readings without input from a user of the sensor.

Yet another object of the invention is reduce the time needed to prepare pressure sensors before implantation.

This invention features a pressure sensor having a substrate and a first, deformable membrane, partially supported by the substrate, which generates a first sensor reading when deformed by pressure. A second membrane is contiguous to the first membrane. When the second membrane is energized, it deforms the first membrane to alter the first sensor reading.

In some embodiments, the first membrane carries a first electrode which forms capacitance with another electrode spaced from the first electrode to generate the first sensor reading. In other embodiments, the first membrane carries at least one strain gauge, such as a piezoresistive element, to generate the first sensor reading when deformed.

In certain embodiments, the second membrane includes piezoelectric material, which may be deposited on the first membrane. The second membrane is energizable by applying a voltage across it. In some embodiments, the substrate and first and second membranes are disposed within a housing that is implantable in a patient.

This invention also features a system for measuring pressure within a patient. The system includes a housing implantable in a patient and containing a substrate. A first circuit has a first, deformable membrane, partially supported by the substrate, which generates a first sensor reading when deformed by pressure. A second circuit includes an energy source and a second membrane contiguous to the first membrane which, when energized by the energy source, deforms the first membrane to alter the first sensor reading.

This invention further features a method of compensating a pressure sensor immersed in a fluid. The method includes obtaining a first sensor reading from a first, deformable membrane within the pressure sensor, and then energizing a second membrane contiguous to the first membrane to deform the first membrane to alter the first sensor reading. A delta response is determined from the first sensor reading and the altered sensor reading, and the delta response is utilized to determine the actual pressure of the fluid.

In some embodiments, energizing the second membrane includes applying a voltage across it. Utilizing the delta response includes retrieving a pressure value corresponding to the delta response. In certain embodiments, the system and method further include generating indicia of the actual pressure such as a visually perceivable pressure value.

BRIEF DESCRIPTION OF THE DRAWINGS

In what follows, preferred embodiments of the invention are explained in more detail with reference to the drawings, in which:

FIG. 1B is a flow chart of calibration steps during production of a sensor according to the present invention using a sequence of known pressures to develop a look-up table of dRx values;

FIG. 2A is a schematic cross-sectional view of a capacitive pressure sensor according to the present invention with no applied external pressure;

FIG. 2B is a view of the sensor of FIG. 2A with external pressure applied;

FIG. 2C is a view of the sensor of FIG. 2B with an energized contiguous membrane according to the present invention;

FIG. 2D is a flow chart of the steps related to FIGS. 2B and 2C;

DETAILED DESCRIPTION OF THE PRESENTLY PREFERRED EMBODIMENTS

Pressure sensors according to the present invention have a substrate and a first, deformable sensor membrane, partially supported by the substrate, which generates a first sensor reading when deformed by pressure. A second membrane is contiguous to the first membrane. When the second, contiguous membrane is energized, it deforms the first membrane to alter the first sensor reading.

Figure 1A:
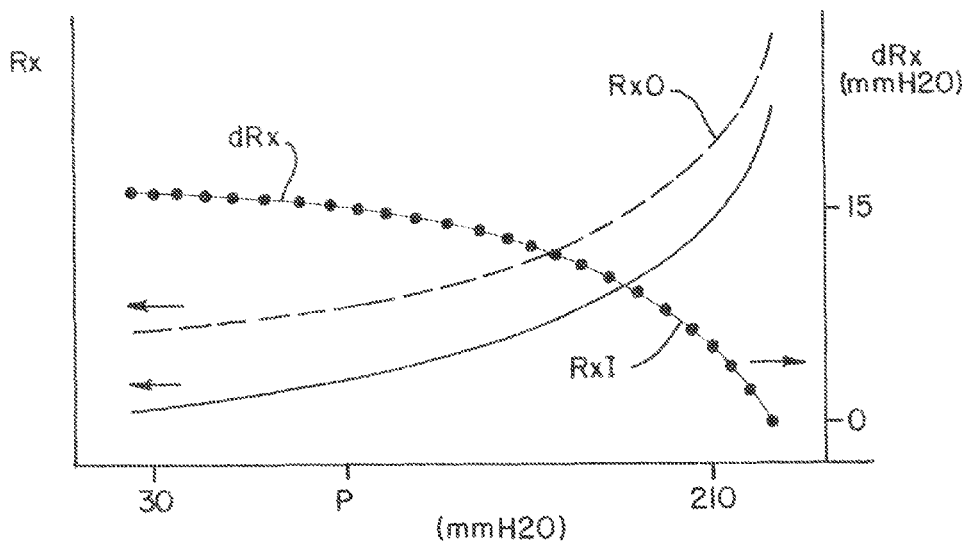
FIG. 1A is a chart showing curves of initial sensor response RxI in solid line, sensor response with offset RxO in dashed line, and delta response dRx in dotted line.

A difference in the response of the pressure sensor with the second, contiguous membrane in an inactive, unenergized state and then in an active, energized state is first utilized under controlled pressure conditions, such as during production of the pressure sensor, to match actual pressures to a plurality of delta response values for that sensor. FIG. 1A depicts an example of an initial sensor response curve RxI, with pressures in mmH2O on the x-axis and obtained sensor readings Rx on the left-hand y-axis, while the second membrane is inactive. This corresponds to steps 100 and 102, FIG. 1B, in which a well-controlled pressure Px is applied to the sensor membrane, such as with a pressure regulator, and the response Rx is read. The second, contiguous membrane is then energized, step 104, such as by applying a precise voltage across it, while maintaining the well-controlled pressure Px of steps 100 and 102, to change the deformation or deflection of the sensor membrane. As described in more detail below, the sensor membrane can be deformed by the energized contiguous membrane in either direction, or even in both directions as desired. The altered sensor response Rxdef is then read, step 106. The second membrane is then deactivated, such as by discontinuing the application of voltage across the second membrane.

A delta response dRx is calculated for the two mechanical states of the sensor membrane at pressure Px by subtracting the initial sensor reading Rx from the energized reading Rxdef, step 108. A data pair of delta response dRx for pressure Px is then stored in memory, step 110. The pressure is then increased by a desired amount y, step 112, and the cycle repeated as indicated by line 114 until a selected number of readings have been taken, using the same energizing voltage each time. A look-up table of data pairs is created in one construction; in another construction, a curve-fitting equation is generated and then stored in the sensor. In either case, one can calculate the pressure P using the value of dRx. In a linear situation, the equation may be:

$$P=a*dRx+b$$

Or in a quadratic curve situation:

$$P=a*drx^2+b*dRx+c$$

A curve dRx is shown in FIG. 1A in dotted line relative to initial, non-offset sensor response curve RxI and an offset curve RxO, shown in dashed line, which is described in more detail below. Representative delta response dRx values in mmH2O are provided in the right-hand y-axis. A realization of the invention is that the curve dRx remains the same even when the sensor membrane readings change due to electronic drift, temperature, or other factors.

A typical pressure range for hydrocephalus monitoring would range from 30 mmH2O to 250 mmH2O. The controlled additional deformation by energizing the contiguous membrane would typically correspond to plus or minus 15 mmH2O. A typical number of cycles in one construction is ten to fifteen over the entire range of pressures that are likely to be experienced by the sensor after implantation. The number of cycles would be increased if a higher accuracy is desired.

One example of delta response values obtained during production at pressure increments of 30 mmH2O is given in Table 1:

| Pressure (P) to measure [mmH2O] | Sensor response from not activated membrane Rx [for instance in kHz for a capacitive senor] | Sensor response rom factivated membrane Rxdef | dRx = Rxdef-Rx [for instance in kHz for a capacitive senor] |
|---|---|---|---|
| 30 | 52 | 73 | 21 |
| 60 | 64 | 83 | 19 |
| 90 | 79 | 94 | 15 |
| 120 | 96 | 104 | 8 |

Cross-sectional views are provided in FIGS. 2A-2C of a capacitive sensor 200 according to the present invention which generates capacitive reading C as a sensor output. Substrates 202 and 204 define between them a closed cavity 206. Substrate 202 carries a first electrode 208 and substrate 204 carries another electrode 210. When the pressure P is at zero, that is, at atmospheric pressure, arrow 214a of FIG. 2A represents the gap between the electrodes 208 and 210 which provides a first capacitance reading C0. When pressure P is Px, then arrow 214b, FIG. 2B, represents a narrower gap which provides a higher capacitance reading Cx.

When a contiguous membrane, not shown separately in FIG. 2C, is energized, then membrane 212 is further deformed from the position of FIG. 2B, represented in phantom by dashed line 216 in FIG. 2C, to further narrow gap 214c to provide a higher capacitance reading Cx plus dCdef. In another construction, the sensor membrane 212 is deformed in the other direction. In yet another construction, membrane 212 is deflected both up and down to create a larger dRx equals dRxup minus dRxdown to increase sensitivity of the system. During manufacture or production of the pressure sensor, the delta response dRx is mapped at different known pressures to generate stored data pairs or to generate a curve-fitting equation as described above.

During actual use of the pressure sensor, the difference between the two mechanical states of sensor membrane 212, depicted in FIGS. 2B and 2C, is utilized as outlined in the flowchart shown in FIG. 2D. A first sensor reading R is obtained, step 230, and then the contiguous membrane is energized, step 232, with the same voltage utilized during production of the sensor so the sensor membrane is deflected in the same defined way. Altered sensor reading Rdef is obtained, step 234, and the delta response dRx is calculated by subtracting reading R from altered reading Rdef, step 236. The actual pressure P is then determined from the value of dRx, step 238. An indicia of actual pressure, such as display of a numerical pressure value, is provided in step 240.

One example of the delta response values that are later utilized in situ is provided using Table 1 above. If, for instance, in an implanted condition the delta response dRx is measured to be 15 kHz, the stored corresponding look-up pressure value is 90 mmH2O. A pressure sensor and system according to the present invention can also interpolate between stored data points. For example, if the delta response dRx is determined to be 20 kHz, then an interpolated pressure value of approximately 45 mmH2O would be generated.

Compensation for sensor drift of 2 mmH2O is illustrated in table 2:

| Pressure to measure [mmH2O] | Sensor response from not activated membrane Rx [for instance in kHz for a capacitive senor] | Sensor response from activated membrane Rxdef | dRx = Rxdef-Rx [for instance in kHz for a capacitive senor] |
|---|---|---|---|
| 30 | 57 = 32 mmH2O | 78 | 21 |
| 60 | 69 = 62 mmH2O | 92 | 19 |
| 90 | 84 = 92 mmH2O | 99 | 15 |
| 120 | 101 = 122 mmH2O | 109 | 8 |

The sensor reading Rx is information that a conventional sensor would provide, which is higher than the actual pressure. By activating a contiguous membrane according to the present invention as illustrated in FIGS. 2A-2D above and described in more detail below, a delta response value is obtained that accurately corresponds to the actual pressure. For example, for an actual pressure of 60 mmH2O, the sensor reading Rx of 69 kHz would falsely indicate a pressure of 62 mmH2O. However, dRx is determined to be 19 kHz which corresponds to the correct pressure of 60 mmH2O. The offset can be calculated as 2 mmH2O and applied to correct further readings or simply stored as a record of sensor performance over time.

Because the delta response dRx is not affected by offset drift, the offset can be calculated whenever desired by determining the difference between reading Rx and delta response dRx. In general, clinicians want accurate readings and so it is preferred to simply display corrected pressure values which represent actual pressures experienced by the sensor, rather than display offset values.

Figure 3:
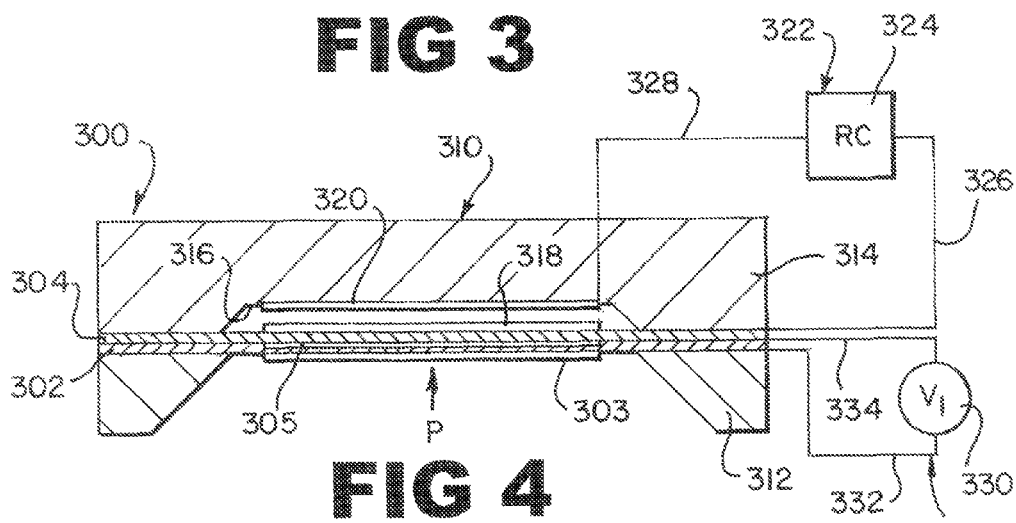
FIG. 3 is a more detailed view of one embodiment of the capacitive sensor of FIGS. 2A-2C in a system with two circuits according to the present invention.
Figure 4:
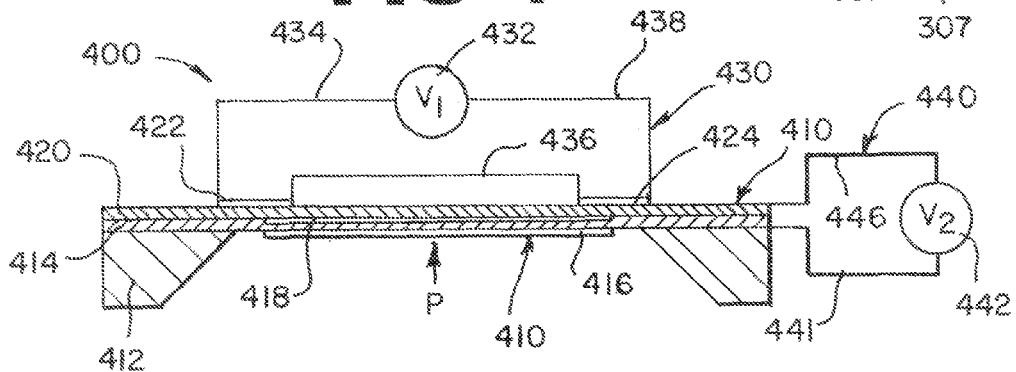
FIG. 4 is a schematic cross-sectional view of one embodiment of a piezoresistive sensor in another system according to the present invention.

The sensor readings and response depend on the type of sensor used, such as capacitive or piezoresistive. A capacitive system 300 according to the present invention is shown in FIG. 3 and a piezoresistive system 400 is shown in FIG. 4. Both systems have membranes made of deformable piezoelectric material and are operated according to the present invention to read a pressure P using techniques as described above. System 300 includes a sensor 310 having a first substrate 312 and a second substrate 314 which define between them a sealed chamber 316. Substrate 312 supports an active piezoelectric layer 302, carrying electrodes 303 and 305 which are part of second circuit 307, and an inactive piezoelectric layer 304 which simply serves as a deformable sensor membrane carrying first capacitive electrode 318. Substrate 314 carries a second capacitive electrode 320. First sensing circuit 322 includes a component 324 having a resonant circuitry RC with connections 326 and 328 to electrodes 318 and 320, respectively, to operate sensor 310 as a capacitive sensor, typically by generating a frequency depending on the capacitance change. Second activation circuit 307 has a component 330 with a voltage source V1 with connections 332 and 334 to contiguous membrane electrodes 303 and 305, respectively, to apply a voltage, typically DC, across contiguous membrane 302 during the activation step according to the present invention.

Piezoresistive system 400 includes a piezoresistive sensor 410 having a substrate 412 with an active piezoelectric layer 412, carrying electrodes 416 and 418, and an inactive piezoelectric layer 420 carrying piezoresistive strain gauges 422 and 424. First sensing circuit 430 includes a component 432 having a DC voltage source V1. Strain gauges 424 and 424 are connected through connections 434, 436 and 438 with component 432 to form a wheatstone bridge piezoresistive sensor circuit. Wheatstone bridges are well known, such as described relative to FIGS. 4 and 6 in U.S. Pat. No. 5,142,912 by Frische, for example. Second activation circuit 440 includes a component 442 having a DC voltage source V2 electrically connected with activation electrodes 416 and 418 through connections 444 and 446, respectively.

In some constructions, the first sensing circuits 322, 430 and the second activation circuits 307, 440 shown in FIGS. 3 and 4 are portions of a larger circuit having memory and a microprocessor programmed to carry out the steps outlined in at least FIG. 2D and preferably also the steps of FIG. 1B. In certain constructions the entire system is contained within a biocompatible housing that is partially or wholly implantable within a human being. Wafer-level manufacturing can be utilized for the components. Any packaging can be utilized for the housing as long as it is mechanically and chemically stable to protect body tissue from possible toxic release of circuitry components and to protect the circuitry from bodily fluids.

Figure 5:
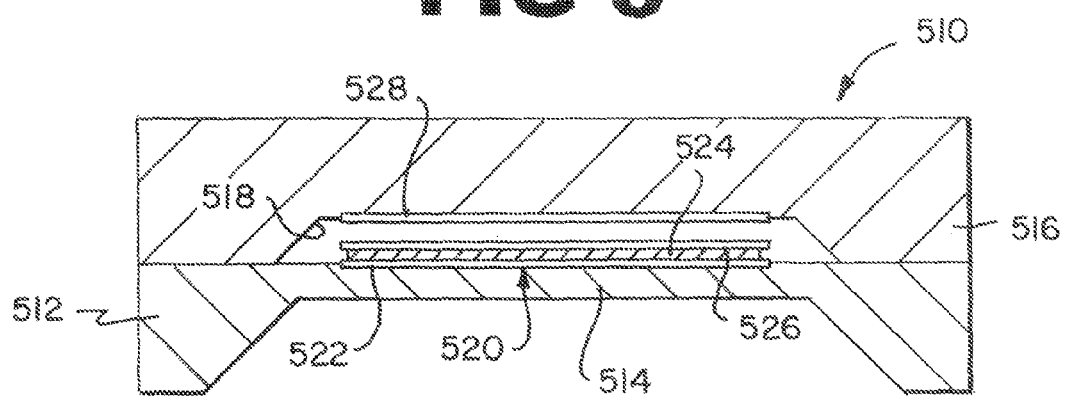
FIGS. 5 and 6 are schematic cross-sectional views of alternative capacitive sensors according to the present invention with deposited contiguous membranes on upper and lower surfaces of the sensor membrane, respectively.
Figure 6:
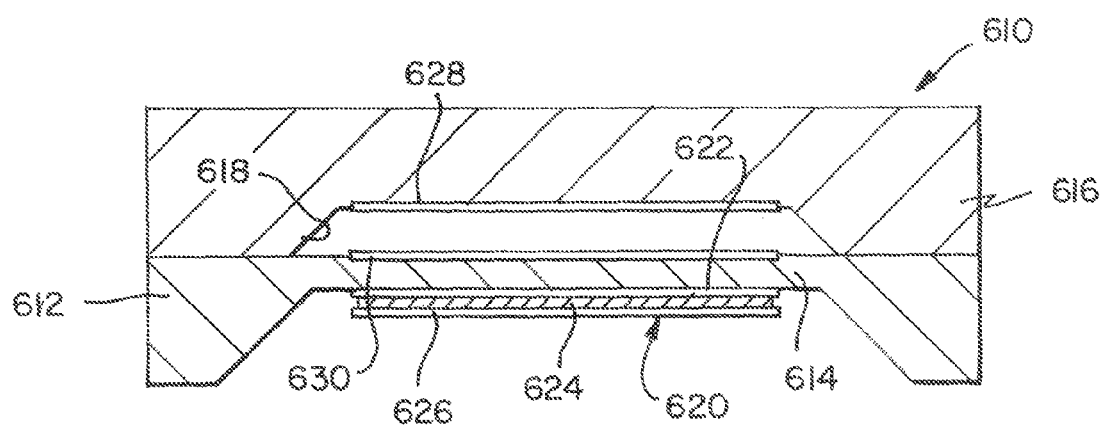

Alternative constructions of capacitive pressure sensors 510 and 610 according to the present invention are shown in FIGS. 5 and 6, respectively, having a piezoelectric layer of a material such as ZnO or AlN, or an electro-active polymer material, deposited on a deformable sensor membrane formed of a non-piezoresistive material such as Si or SiN. A piezoelectric material always deforms in the same way when the same voltage is applied, and electro-active polymer material always swells in the same way when the same voltage is applied each time. Sensor 510 has substrates 512 and 516 which define between them a closed cavity 518. Substrate 512 has a thinned region which serves as deformable sensing membrane 514. A contiguous membrane 520 is formed with electrode 522 that is used simultaneously for both capacitance sensing, together with spaced electrode 528 carried by substrate 516, and for activating piezoelectric material 524, together with electrode 526.

Sensor 610, FIG. 6, has substrates 612 and 616 which define sealed cavity 618. Contiguous membrane 620 is formed on the lower surface of sensing membrane 614 with electrodes 622 and 626 for activating piezoelectric material 624. The upper surface of sensing membrane 614 carries capacitive electrode 630 which forms a capacitance with electrode 628 carried by a lower surface of substrate 616. Sensors 510 and 610 may be operated as described above in relation to FIG. 3.

Figure 7:
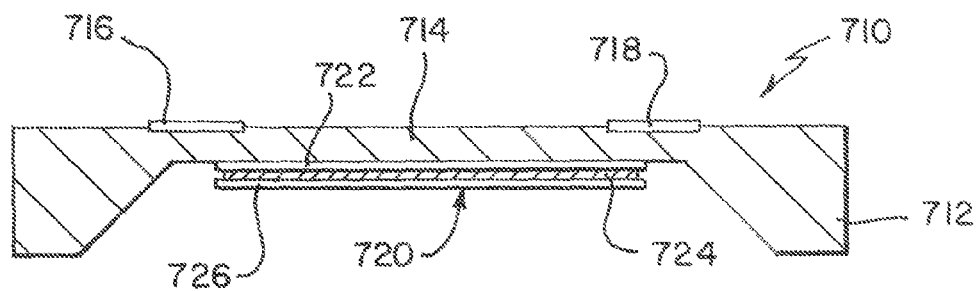
FIG. 7 is a schematic cross-sectional view of an alternative piezoresistive sensor according to the present invention with deposited contiguous membrane.

A piezoresistive sensor 710, FIG. 7, includes a substrate 712 with a thinned region serving as a deformable sensing membrane 714. Piezoresistive elements 716 and 718 serve as strain gauges, such as described above in relation to FIG. 4. Deposited contiguous membrane 720 includes electrode 722 contacting the lower surface of sensing membrane 714, piezoelectric material 724, and electrode 726. In an alternative construction, contiguous membrane 720 is deposited on the same surface as piezoresistive elements 716 and 718.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A pressure sensor comprising:
   a substrate;
   a first, deformable membrane, partially supported by the substrate, which generates a first sensor reading when deformed by pressure; and
   a second deformable membrane contiguous to and touching the first membrane which, when energized, deforms and deforms the first membrane to alter the first sensor reading;
   wherein the first membrane carries a first electrode which forms capacitance with another electrode spaced from the first electrode to generate the first sensor reading.

2. The pressure sensor of claim 1 wherein the first membrane carries at least one strain gauge to generate the first sensor reading when deformed.

3. The pressure sensor of claim 2 wherein the strain gauge includes a piezoresistive element.

4. The pressure sensor of claim 1 wherein the second membrane includes piezoelectric material.

5. The pressure sensor of claim 4 wherein the piezoelectric material is deposited on the first membrane.

6. The pressure sensor of claim 1 wherein the second membrane is energizable by applying a voltage across it.

7. The pressure sensor of claim 1 wherein the substrate and first and second membranes are disposed within a housing that is implantable in a patient.

8. A system for measuring pressure within a patient, comprising:
   a housing implantable in a patient and containing a substrate;
   a first circuit including a first, deformable membrane, partially supported by the substrate, which generates a first sensor reading when deformed by pressure; and
   a second circuit including an energy source and a second deformable membrane, contiguous to and touching the first membrane which, when energized by the energy source, deforms and deforms the first membrane to alter the first sensor reading;
   wherein the first membrane carries a first electrode which forms capacitance with another electrode spaced from the first electrode to generate the first sensor reading.

9. The system of claim 8 wherein the first membrane carries at least one strain gauge to generate the first sensor reading when deformed.

10. The system of claim 8 wherein the second membrane includes piezoelectric material.

11. The system of claim 8 wherein the second circuit applies a voltage across the second membrane energize it.

12. A method of compensating a pressure sensor immersed in a fluid, comprising:
    obtaining a first sensor reading from a first, deformable membrane within the pressure sensor;

energizing a second deformable membrane contiguous to and touching the first membrane to deform and deform the first membrane to alter the first sensor reading;

determining a delta response from the first sensor reading and the altered sensor reading; and utilizing the delta response to determine the actual pressure of the fluid.

13. The method of claim 12 wherein energizing the second membrane includes applying a voltage across it.

14. The method of claim 12 wherein utilizing the delta response includes retrieving a pressure value corresponding to the delta response.

15. The method of claim 12 further including generating indicia of the actual pressure.

16. A pressure sensor comprising:

a substrate;

a first, deformable membrane, partially supported by the substrate, which generates a first sensor reading when deformed by pressure; and a second deformable membrane contiguous to and touching the first membrane which, when energized, deforms and deforms the first membrane to alter the first sensor reading;

wherein the first membrane carries at least one strain gauge to generate the first sensor reading when deformed.

17. A pressure sensor comprising:

a substrate;

a first, deformable membrane, partially supported by the substrate, which generates a first sensor reading when deformed by pressure; and a second deformable membrane contiguous to and touching the first membrane which, when energized, deforms and deforms the first membrane to alter the first sensor reading;

wherein the substrate and first and second membranes are disposed within a housing that is implantable in a patient.

* * * * *